United States Patent
Nicolai et al.

(10) Patent No.: US 8,571,674 B2
(45) Date of Patent: Oct. 29, 2013

(54) MULTIMODAL AUDITORY FITTING

(75) Inventors: Jochen Nicolai, Oberwil (CH); Ernst von Wallenberg, Muelheim, DE (US)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/559,015

(22) Filed: Jul. 26, 2012

(65) Prior Publication Data
US 2012/0290045 A1    Nov. 15, 2012

Related U.S. Application Data

(62) Division of application No. 11/635,693, filed on Dec. 8, 2006, now Pat. No. 8,265,765.

(30) Foreign Application Priority Data

Dec. 8, 2005 (AU) .................................. 2005906898

(51) Int. Cl.
*A61N 1/18* (2006.01)

(52) U.S. Cl.
USPC .................. 607/55; 607/137; 607/56; 607/57

(58) Field of Classification Search
USPC .................... 607/55–57, 137; 623/10, 24–25; 606/109
See application file for complete search history.

(56) References Cited

U.S. PATENT DOCUMENTS

| | | |
|---|---|---|
| 3,751,605 A | 8/1973 | Michelson |
| 4,051,330 A | 9/1977 | Cole |
| 4,400,590 A | 8/1983 | Michelson |
| 4,819,647 A | 4/1989 | Byers et al. |
| 5,033,090 A | 7/1991 | Weinrich |
| 5,201,006 A | 4/1993 | Weinrich |
| 5,204,917 A | 4/1993 | Arndt et al. |
| 5,357,576 A | 10/1994 | Arndt |
| 5,601,617 A | 2/1997 | Loeb et al. |
| 5,606,621 A | 2/1997 | Reiter et al. |

(Continued)

FOREIGN PATENT DOCUMENTS

| | | |
|---|---|---|
| EP | 1 338 301 A1 | 8/2003 |
| WO | 97/09863 A1 | 3/1997 |
| WO | 02/082982 A1 | 10/2002 |

OTHER PUBLICATIONS

Boretzki, "Quantification of significant sound quality attributes in the context of hearing instrument fine tuning", Phonak Hearing Systems, Focus #25, 2000, 11 Pages.

(Continued)

*Primary Examiner* — Joseph Stoklosa
(74) *Attorney, Agent, or Firm* — Kilpatrick, Townsend & Stockton, LLP.

(57) ABSTRACT

The present invention provides for fitting a multimodal hearing system to a recipient. Such fitting may include determining a desired perception for an input signal, receiving a measurement of a perception evoked by applying to the recipient one or more stimulation signals that correspond to the input signal, wherein the one or more stimulation signals applied using two or more stimulation modes, and each stimulation signal is determined using stimulus mode weighting, and adjusting one or more of the stimulus mode weightings based on the difference between the measured evoked perception and the desired perception. A multimodal hearing system is able to stimulate using an acoustic, electrical, mechanical mode and/or photo effect mode.

21 Claims, 10 Drawing Sheets

(56) References Cited

U.S. PATENT DOCUMENTS

| | | | |
|---|---|---|---|
| 5,626,629 A * | 5/1997 | Faltys et al. | 607/57 |
| 5,938,691 A | 8/1999 | Schulman et al. | |
| 6,129,753 A | 10/2000 | Kuzma | |
| 6,157,861 A | 12/2000 | Faltys et al. | |
| 6,219,580 B1 | 4/2001 | Faltys et al. | |
| 6,231,604 B1 | 5/2001 | von Ilberg | |
| 6,249,704 B1 | 6/2001 | Maltan et al. | |
| 6,289,247 B1 | 9/2001 | Faltys et al. | |
| 6,522,764 B1 | 2/2003 | Bøgeskov-Jensen | |
| 6,549,814 B1 | 4/2003 | Strutz et al. | |
| 6,611,718 B2 | 8/2003 | Zilberman et al. | |
| 6,658,125 B1 | 12/2003 | Batting | |
| 6,697,674 B2 | 2/2004 | Leysieffer | |
| 6,700,983 B1 | 3/2004 | Bøgeskov-Jensen et al. | |
| 6,728,578 B1 | 4/2004 | Voelkel | |
| 6,748,094 B1 | 6/2004 | Tziviskos et al. | |
| 6,754,537 B1 | 6/2004 | Harrison et al. | |
| 7,016,512 B1 | 3/2006 | Feeley et al. | |
| 7,043,303 B1 | 5/2006 | Overstreet | |
| 7,110,562 B1 | 9/2006 | Feeley et al. | |
| 7,496,406 B1 | 2/2009 | Segel et al. | |
| 7,561,920 B2 | 7/2009 | Faltys et al. | |
| 2002/0012438 A1 | 1/2002 | Leysieffer et al. | |
| 2002/0095194 A1 | 7/2002 | Charvin et al. | |
| 2002/0138115 A1 | 9/2002 | Baumann et al. | |
| 2004/0010181 A1 | 1/2004 | Feeley et al. | |
| 2004/0133250 A1 | 7/2004 | Ball et al. | |
| 2005/0055069 A1 | 3/2005 | Franck | |
| 2005/0245991 A1 | 11/2005 | Faltys et al. | |
| 2007/0135862 A1 | 6/2007 | Nicolai et al. | |

OTHER PUBLICATIONS

"Claro Loudness Perception Profile", Phonak Hearing Systems, 2000, 6 Pages.

Russ et al., "Belton's Adaptive Fitting Algorithm: Combining Loudness Normalisation and Loudness Equalisation to Achieve Target Gain.", audiologyonline.com, Sep. 4, 2001, 6 Pages.

* cited by examiner

MULTIMODAL AUDITORY FITTING

CROSS-REFERENCE TO RELATED APPLICATIONS

This application is a divisional of U.S. patent application Ser. No. 11/635,693, filed on Dec. 8, 2006, now U.S. Pat. No. 8,265,765, issued on Sep. 11, 2012 which claims priority from Australian Provisional App. No. 2005906898, entitled "Method and Device For Adaptive Multi Modal Auditory Fitting," filed Dec. 8, 2005, which is hereby incorporated by reference herein.

BACKGROUND

1. Field of the Invention

The present invention relates auditory fitting, and more particularly, to auditory fitting for multimodal stimulation device.

2. Related Art

Hearing loss is generally of two types, namely conductive and sensorineural. Conductive hearing loss occurs when the normal mechanical pathways for sound to reach the hair cells in the cochlea are impeded, for example, by damage to the ossicles. In such cases, the hearing loss may often be compensated by the use of hearing instruments, which amplify a microphone signal. Hearing instruments deliver acoustic or mechanical energy to the ear. This may be through a column of air to the eardrum, or coupling of a transducer to the tympanic membrane, the skull, an ossicle, the round or oval window or any other structure suitable to lead the imposed mechanical energy to the hydro-mechanical system in the inner ear.

Sensorineural hearing loss, however, is due to the absence or destruction of the hair cells in the cochlea that are needed to transduce acoustic signals into auditory nerve impulses. Individuals suffering from a severe or profound form of this type of hearing loss are unable to derive benefit from these hearing instruments described above. This is because the natural mechanisms for transducing sound energy into auditory nerve impulses have been damaged. In such cases, hearing prosthetic implants, such as Cochlear™ and Nucleus™ implants produced by Cochlear Limited of Australia, have been developed to provide the sensation of hearing to such individuals. In this kind of hearing prosthetic implants, electrical stimulation is provided via stimulating electrodes positioned as close as possible to the nerve of the auditory nerve, essentially bypassing the hair cells in a normally functioning cochlea. The application of a stimulation pattern to the nerve endings causes impulses to be sent to the brain via the auditory nerve, resulting in the brain perceiving the impulses as sound.

The treatment of both of the noted types of hearing loss has been quite different, relying on two quite different principles to deliver sound signals to be perceived by the brain as sound. It is relatively common in hearing impaired individuals to experience severe sensorineural hearing loss for sounds in the high frequency range, and yet still be able to discern sounds in the middle to low frequency range, through the use of a hearing instrument, or naturally. Traditionally, in the majority of such cases, the recipient would only receive treatment to preserve and improve the hearing for the middle to low frequency sounds, most probably via a hearing instrument, and little would be done to attempt to restore the severe hearing loss for the high frequency sounds.

More recently, there has been an increased interest in hybrid device, such as Electro-Acoustical Stimulation (EAS), in which electrical stimulation of the cochlea is used in conjunction with acoustical stimulation. Such hybrid combination device may provide the recipient with the ability to derive benefit from both hearing instruments and prosthetic implants as described in above. The hearing instrument amplifies low frequencies of a sound signal while the hearing prosthesis electrically stimulates the middle and high frequencies of that sound signal. However, the transfer function of each stimulation component of such a hybrid system requires distinguished adjustment to be optimized for the recipient.

SUMMARY

In a first aspect of the present invention, there is provided a method for fitting a multimodal hearing system for a recipient comprising: determining a desired perception for an input signal; receiving a measurement of a perception evoked by applying to the recipient one or more stimulation signals that correspond to the input signal, wherein the one or more stimulation signals applied using two or more stimulation modes, and each stimulation signal is determined using stimulus mode weighting; and adjusting one or more of the stimulus mode weightings based on the difference between the measured evoked perception and the desired perception. The method may be implemented in a clinical program system or a computer program product on a computer readable medium.

In a second aspect of the present invention, there is provided a system for fitting a multimodal hearing system to a recipient comprising an input device for obtaining a measurement of a perception evoked by applying to the recipient one or more stimulation signals that correspond to an input signal, wherein the one or more stimulation signals applied using two or more stimulation modes, and each stimulation signal is determined using stimulus mode weighting; and a processor for adjusting one or more of the stimulus mode weighting based on the difference between the measured evoked perception and a desired perception for the input signal.

In a third aspect of the present invention, there is provided a computer-readable medium having a computer program for fitting a multimodal hearing system to a recipient, said computer program comprising: logic configured to determine a desired perception for an input signal; logic configured to retrieve a measurement of a perception evoked by applying to the recipient one or more stimulation signals that correspond to the input signal, wherein the one or more stimulation signals applied using two or more stimulation modes, and each stimulation signal is determined using stimulus mode weighting; and logic configured to adjust one or more of the stimulus mode weighting based on the difference between the measured evoked perception and the desired perception.

BRIEF DESCRIPTION OF THE DRAWINGS

The invention will be described in conjunction with the accompanying drawings, in which.

DETAILED DESCRIPTION

Figure 1:
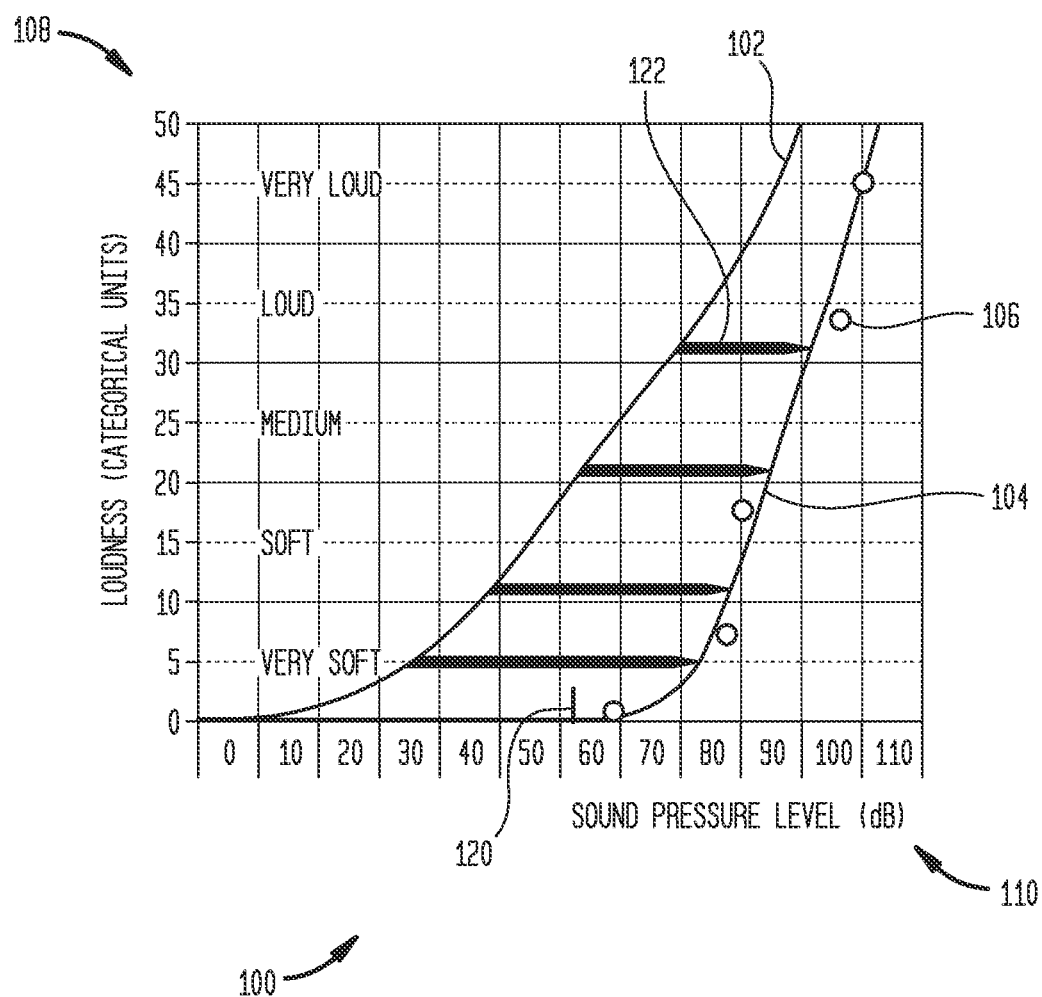
FIG. 1 is graph from a loudness perception model used with embodiments of the present invention.

Aspects of the present invention are generally directed to fitting a multimodal hearing system. A multimodal hearing system applies stimulation signals in accordance with two or more stimulation modes. For example, when implementing an acoustic stimulation mode, the hearing system generates acoustic or sound signals; when implementing an electrical stimulation mode, the hearing system generates electrical stimulation signals; and when implementing a mechanical stimulation mode, the hearing system directly applies one or more forces to the recipient's ear or surrounding anatomy.

In one embodiment of the present invention, the fitting process involves determining a desired perception or desired recipient response for an input signal. An input signal may be any acoustic, electrical or other signal that is, represents or is related to sound or sound perception. Typically, the fitting process determines the desired perception using one or more models of hearing, including perceptual models. Perceptual models are well-known techniques for determining the characteristics of each applied stimulation signal (acoustic, electrical and/or mechanical) to achieve the desired perception. These characteristics are utilized in a feedback process to determine how to adjust the specific transfer function or weighting for all stimulation mode offered by the multimodal hearing system. This adjustment of relative weights of the applied stimulation signal characteristics is iteratively performed to produce a transfer function of the multimodal hearing system that gives a perception as close as possible to the desired perception.

The adjustment is based on a comparison of the desired perception and received measured perception or actual perception. The perception is the recipient's response to sound or stimulation. The measured perception is the recipient's perception evoked in response to the application of one or more stimulation signals. Initially, the evoked perception is the response to stimulation signals that correspond to the input signal, treated by a pre-set of an overall transfer function of the multimodal hearing system. The adjusted transfer functions, also referred to stimulation mode weighting, create further adjusted stimulation signals which are applied and measured in a similar iterative process. This iterative process minimizes the difference between actual perception and desired perception. Once an acceptable result is achieved, the stimulation mode transfer function is stored in a user-specific program or MAP for operation use. Such fitting methods may be performed by a clinician programming system, computer program product or computer logic.

When a recipient first receives a multimodal hearing system, the system must be fitted or adjusted to the recipient. Since each recipient experiences different sound perceptions, fitting is necessary prior to using the hearing system after provision. It is noted that fitting may also be periodically required during the operational use of the multimodal hearing system. The effectiveness of a multimodal hearing system depends not only on the device itself, but also on the way in which the device is configured or "fit" to the recipient. As used for the purposes of this invention the terms "fit," "adjust," "program," "fitting," "adjusting," "mapping," or "programming," relate making electronic or software programming changes to the multimodal hearing system. It may also include instructions to the operator to alter hardware characteristic such as the vent size of an ear mold. The characteristics available for adjustment may vary depending on the multimodal hearing system and may include one or more of the following: number of channels, T-levels, C-levels, gain, frequency of stimulation, compression characteristic, type of strategy, etc. Typically fitting is performed with a specialist, i.e. audiologist or hearing clinician, who adjusts parameters to ensure that the multimodal hearing system performs for its intended function for that particular recipient. Alternatively, the invention may support self fitting of a recipient, where the recipient directly interacts with a computer system. The results of the fitting process may be saved as a set of instructions, e.g. in a user-specific program or MAP, and stored in a signal processor that the recipient uses. A multimodal hearing system that is optimized may increase the recipient's acceptance and lead to maximal benefit of the multimodal prosthesis.

As noted, aspects of the present invention are generally directed to fitting a multimodal system. Certain embodiments refine or adjust the stimulus mode transfer functions, also referred to stimulus mode weighting (SMW), by translating the differences in the psychophysical domain between the measured evoked perception and the desired perception into the signal processing domain. Thus, the unadjusted stimulation signal may evoked one perception in a recipient, while the adjusted stimulation signal refined with the stimulus mode weightings and stimulus mode transfer functions may evoked a different perception.

By providing for use of pre-defined perceptual models to refine the stimulus mode transfer function, embodiments of the present invention allow substantially automated fitting of the multimodal system to the recipient. Such automation is particularly needed in multimodal system fitting, as a high degree of specialization is required for a clinician to have sufficient expertise to manually fit a device having one mode, let alone a multimodal system. These embodiments allow fitting by the clinician without requiring the clinician to have in-depth knowledge of each mode of the multimodal hearing system being fitted. One aim of certain embodiments of the present invention is to deskill the task of fitting a multimodal system, such that the clinician of the multimodal system does not need to know about the different stimulation modes, e.g. does not need to decide when to use acoustic mode and when to use electric stimuli mode. Thus, an advantage of the embodiments provides the clinician a tool determine the amount of stimulation of each mode of a multimodal hearing system.

Further, embodiments may eliminate the need learning different fitting approaches for different types of hearing stimulus devices, including multimodal hearing system. Such embodiments may separate the clinician from the complexities involved in conforming to such perception models, and thus may save training effort and increase the number of clinicians able to adjust more complex hearing systems such as multimodal hearing systems, e.g. electro-acoustic sound processors.

The need to manage the different stimulation modes continues after the initial turn on the multimode hearing system and embodiments of the present invention may be used during any fitting procedure. Further, by obtaining a measure of the particular recipient's evoked perception, embodiments may achieve individually optimal transfer functions of a multimodal hearing system, without relying on statistical assumptions or an average response.

Embodiments of the present invention may be implemented in a computer program product on a computer readable medium. The computer readable medium includes optical and magnetic disks as well as memory, flash memory, tape drives, floppy disks, hard drives, etc. The computer program product may also be downloaded through a network of computers. A computing device may read the program from the computer readable medium and implement embodiments of the present invention.

Embodiments of the present invention may use any one of a plurality of perception models to determine a desired perception and provide rules for modifying the stimulus mode transfer functions through weighting. Such a perceptual model may comprise one or more existing models, such as loudness models, pitch models and other models. Further, depending on the rules of the selected perceptual models, parameters such as, e.g. frequency to channel allocation, in the electrical mode of the system may be adjusted when specifying the optimal mode specific transfer functions. A perceptual model may be selected from a library of models, which are pre-defined, based on user input, based on a-priori information of the recipient, based on information linked to the chosen input signal and/or available stimulation modality.

Examples of various perception models include those described in the following references: Kiessling et. al., "Adaptive Fitting of Hearing Instruments by Category Loudness Scaling," Scand. Audiol. 1996, pg. 153-160; "Claro Loudness Perception Profile" of Phonak, CU/BGS_LP-P_GB/0200; Dian Russ, "Belton's Adaptive Fitting Algorithm: Combining Loudness Normalisation and Loudness Equalisation to Achieve Target Gain," audiologyonline.com, (Sep. 4, 2001); Moore et al., "Comparison of two adaptive procedures for fitting a multi-channel compression hearing aid." Int'l J. Audiol. Vol. 44, No. 6 (Jun. 2005) pages 345-57; Boretzki, "Quantification of significant sound quality attributes in the context of hearing instrument fine tuning," Phonak GmbH, Focus #25; U.S. Pat. Pub. No. US2005/0055069; Int'l Pub. No. WO2002/017678; McKay, et al., "A practical method of predicting the loudness of complex electrical stimuli," J Acoust Soc Am Vol. 113, No. 4 (2003) pages 2054-2063; and Moore and Glasberg, "A Model of Loudness Perception Applied to Cochlear Hearing Loss," Auditory Neuroscience, Vol. 3 (1997) pages 289-311; ISO 532 (Zwicker model) (1975); and Moore & Glasberg, "A Model for the Prediction of Thresholds, Loudness and Partial Loudness," Journal of the Audio Engineering Society, vol. 45, no. 4 (1997) pages 224-240. The entire contents and disclosure of the above-listed references are hereby incorporated by reference. Various other models of normal hearing may also be used in conjunction with embodiments of the present invention.

Other models that may be used to determine a desired perception or recipient response may include an input-output model of an objective evoked response. This input-model may be selected from a library of input-output models.

One type of perception model may be a loudness perception model. Loudness perception models may be used with embodiments of the present invention that use the "categorical loudness units" derived by loudness scaling, instead of sone. The fitting procedure using a loudness perception model may be repeated for several center frequencies and presentation levels across the auditory field. For example, in the field of hearing instruments fitting a perception model may use adaptive fitting processes based on loudness scaling. In these models the gain of a hearing instrument, at a given input frequency and sound pressure level, is determined by the difference between the desired loudness and the actual perceived loudness with the hearing instrument. An adaptive process derived from a Claro Loudness Perception Profile from Phonak is shown in FIG. 1.

In FIG. 1 a graph 100 shows a desired perception curve 102 and an evoked perception curve 104. Graph 100 shows an evoked perception curve 104 for recipient with sensorineural hearing loss created by measured data points 106. Note that evoked perception curve 104 is steeper and laterally displaced compared to the curve for normal hearing showed by desired perception curve 102. Depending on the type of hearing loss, the shape of evoked perception curve 104 may be different or shifted. The subjective perceptions of the recipient are measured on the vertical axis 108 using a numerical scale and/or categories of very soft, soft, medium, loud or very loud. Along the X-axis 110 the sound pressure level (SPL) is measured in decibels (dB). The hearing threshold 120 is a minimum SPL that the recipient perceives. The arrows 122 in FIG. 1 illustrate the gain at each input sound pressure level necessary to compensate the recipient's hearing loss. The larger the length of the arrow 122, the larger the desired gain increase. FIG. 1 shows smaller gain increases at higher loudness levels due to the recruitment phenomenon. Note that the lower limit of the loudness level categories may be inaudible.

In other perception models for hearing instrument fitting, the adaptive fitting process may characterize evoked perceptions quantitatively and qualitatively using multiple dimensions, such as loudness, tonal quality and clarity, e.g. of speech. Still other perception models may point to signal processing parameters such as gain, compression and attack time in the transfer function of the hearing instrument that need adjustment to optimize perceived sound quality and speech understanding.

Other adaptive fitting models and concepts apply paired comparison and genetic algorithms to converge to an optimal transfer function or use phonetic mismatch analysis. A genetic algorithm is an adaptive procedure based on a model of biological evolution, which can be used to find optimal solutions to a problem. One example of a genetic algorithm is described in U.S. Pat. No. 6,879,860 and U.S. application Ser. No. 10/963,594, the entire contents and disclosure of which is hereby incorporated by reference. The procedure implements aspects of evolution, including "natural selection," "procreation with inheritance," and "random mutation." The underlying premise is that the evolutionary process will, over multiple generations, produce an optimal "organism;" that is, an organism that it is most likely to survive and procreate. Combining an iterative approach with more sophisticated processes, such as above mentioned genetic algorithms, may speed the fitting process.

Still further automatic fitting systems use patient specific data, for example from automatically or semi-automatically obtained objective measures, described in U.S. Pat. Nos. 6,915,166 and 6,751,505, the entire contents and disclosures of which is hereby incorporated by reference. These fitting systems apply a prescriptive formula to obtain the stimulus mode weighting for adjusting the transfer function which is expected to be optimal, based on the average experience from a large patient sample. The objectively obtained data might be complemented by other a-priori information, such as demographic data, or by adding few simple parameterized behavioral measurements. One example of a model using a-priori information is described in EP Patent No. 1,338,301, the entire contents and disclosures of which is hereby incorporated by reference.

Perception models designed for specific types of recipients, such as children, are described in US Patent Pub. No. 2005/0055069, the entire contents and disclosures of which are hereby incorporated by reference.

As noted, multimodal prostheses include devices that are operable to apply one or more of the following stimulation modes: acoustic stimulation; electrical stimulation; and direct mechanical stimulation. Acoustic stimulation may be via the natural hearing passage from the outer ear through to the cochlea. Additionally or alternatively, acoustic stimulation may be amplified via an acoustic hearing instrument. Electrical stimulation may be via an electrode array inserted in or near the cochlea. Direct mechanical stimulation may be via an actuator coupled to an anatomical structure suitable to transfer the mechanical/acoustical stimulation to the inner ear fluid system. The actuators, electrodes and processors may be mechanically grouped in various housing configurations or within a single housing. Various mechanical stimulations are described in U.S. Pat. Nos. 5,814,095, 5,906,635, 6,005,955, and 6,547,715, the entire contents of which is hereby incorporated by reference. Another mode of the multimodal hearing system may comprise a photo effect mode.

Various multimodal prostheses examples are described in U.S. Pat. Nos. 6,611,718, and 6,565,503, the entire contents of which is hereby incorporated by reference. Other examples of multimodal implants include those described and shown in co-pending commonly owned U.S. Ser. No. 09/896,836, filed on Jul. 2, 2001, Ser. No. 11/125,334, filed on May 10, 2005 and Ser. No. 11/434,929, filed on May 17, 2006, the entire contents and disclosures of which is hereby incorporated by reference.

Figure 2A:
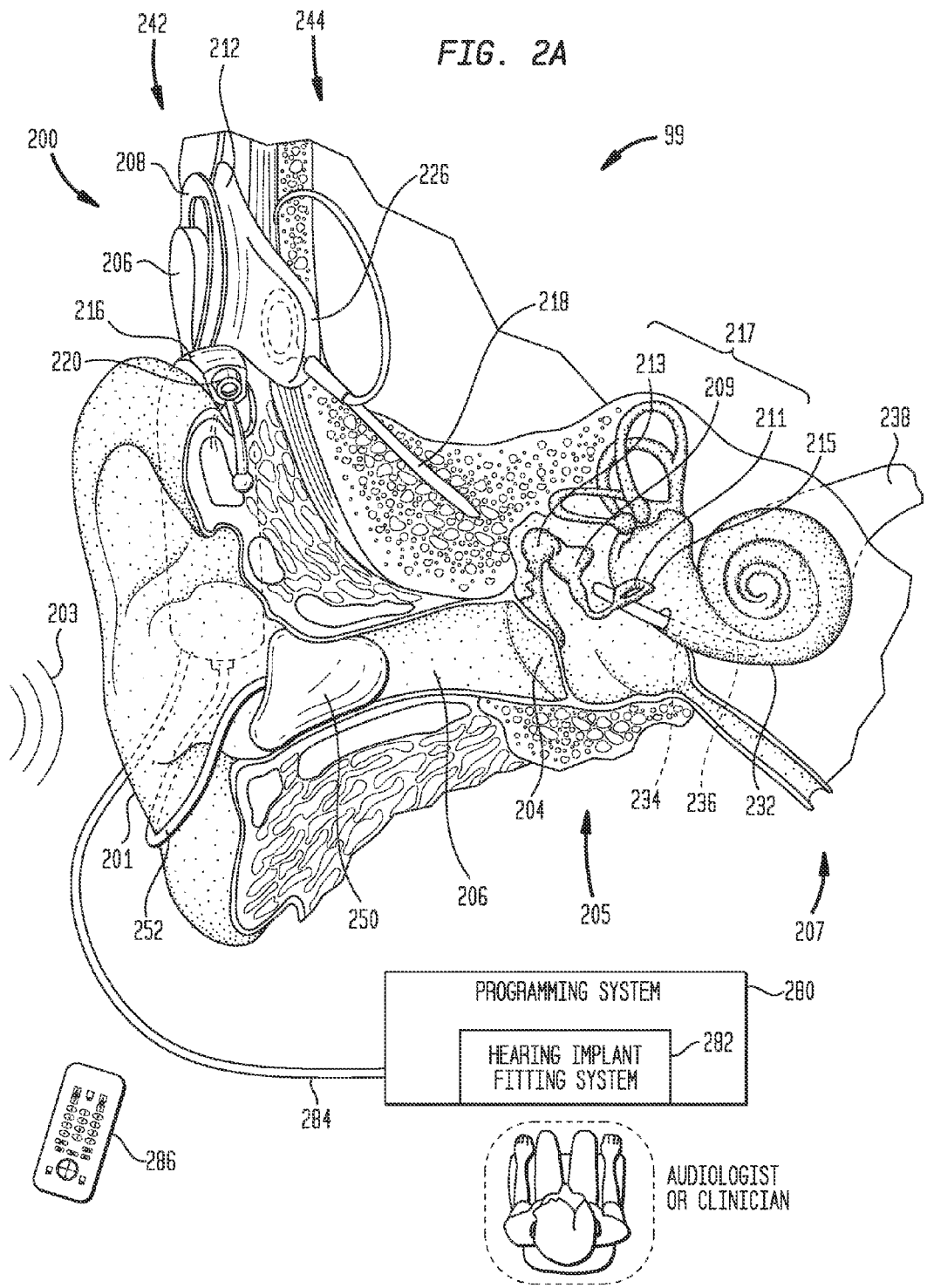
FIG. 2A is a perspective view of an exemplary multimodal system suitable for implementing embodiments of the present invention.

FIG. 2A is a perspective view of an exemplary multimodal prosthesis in which the present invention may be implemented. The ear 99 includes outer ear 201, middle ear 205 and inner ear 207 are described next below, followed by a description of an implanted multimodal system 200. Multimodal system 200 provides multiple types of stimulation, i.e. acoustic, electrical and/or mechanical. These different stimulation modes may be applied ipsilaterally or contralaterally. In the embodiment shown in FIG. 2, multimodal implant 200 provides acoustic and electrical stimulation, although other combinations of modes are contemplated by this invention.

In a person with normal hearing or a recipient with residual hearing, an acoustic pressure or sound wave 203 is collected by outer ear 201 (that is, the auricle) and channeled into and through ear canal 206. Disposed across the distal end of ear canal 206 is a tympanic membrane 204 which vibrates in response to acoustic wave 203. This vibration is coupled to oval window, fenestra ovalis, 215 through three bones of middle ear 205, collectively referred to as the ossicles 217 and comprising the malleus 213, the incus 209 and the stapes 211. Bones 213, 209 and 211 of middle ear 205 serve to filter and transfer acoustic wave 203, causing oval window 215 to articulate, or vibrate. Such vibration sets up waves of fluid motion within cochlea 232. Such fluid motion, in turn, activates tiny hair cells (not shown) that line the inside of cochlea 232. Activation of the hair cells causes appropriate nerve impulses to be transferred through the spiral ganglion cells (not shown) and auditory nerve 238 to the brain (not shown), where such pulses are perceived as sound.

Figure 2B:
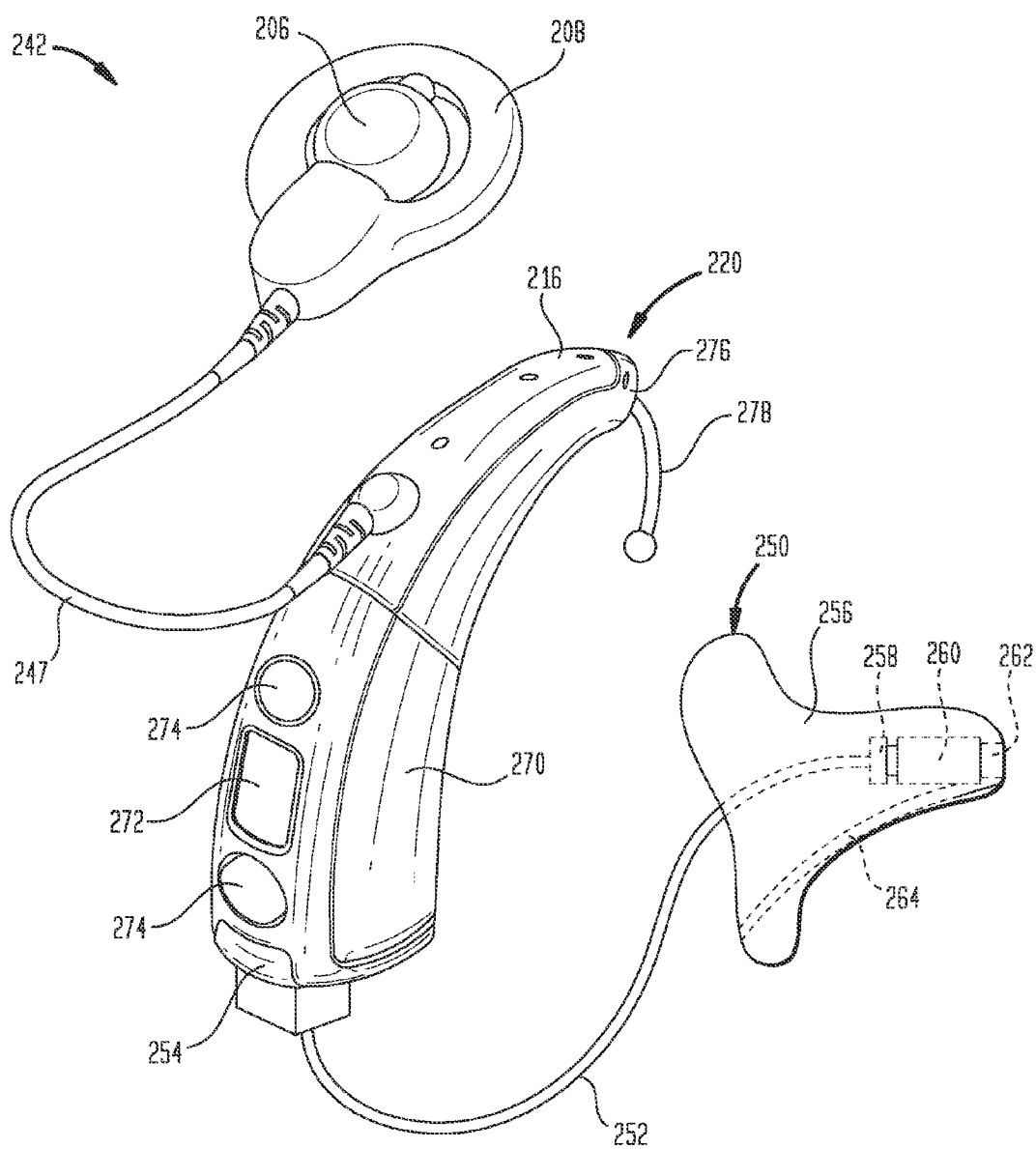
FIG. 2B is a perspective view of the external components shown in FIG. 2A.

In individuals with a hearing deficiency, who may have some residual hearing, an implant or hearing instrument may improve that individual's ability to perceive sound. Multimodal prosthesis 200 may comprises external component assembly 242 which is directly or indirectly attached to the body of the recipient, and an internal component assembly 244 which is temporarily or permanently implanted in the recipient. External component assembly is also shown in FIG. 2B. In embodiments of the present invention, components in the external assembly 242 may be included as part of the implanted assembly 244, and vice versa. Also, embodiments of the present invention may be used with implanted multimodal system 200 which are fully implanted.

External assembly 242 typically comprises a sound transducer 220 for detecting sound, and for generating an electrical audio signal, typically an analog audio signal. In this illustrative embodiment, sound transducer 220 is a microphone. In alternative embodiments, sound transducer 220 may comprise, for example, more than one microphone, one or more a telecoil induction pickup coils or other device now or later developed that may detect sound and generate electrical signals representative of such sound.

External assembly 242 also comprises a signal processing unit 216, a power source (not shown), and an external transmitter unit 206. External transmitter unit 206 comprises an external coil 208 and, preferably, a magnet (not shown) secured directly or indirectly to the external coil 208. Signal processing unit 216 processes the output of microphone 220 that is positioned, in the depicted embodiment, by outer ear 201 of the recipient. Signal processing unit 216 generates coded signals, referred to herein as a stimulation data signals, which are provided to external transmitter unit 206 via a cable 247 and to the receiver in the ear 250 via cable 252. Signal processing unit 216 is, in this illustration, constructed and arranged so that it can fit behind outer ear 201 in a BTE (behind-the-ear) configuration, but may also be worn on different parts of the recipient's body or clothing.

In some embodiments, signal processor 216 may produce electrical stimulations alone, without generation of any acoustic stimulation beyond those that naturally enter the ear. While in still further embodiments, two signal processors may be used. One signal processor is used for generating electrical stimulations in conjunction with a second speech processor used for producing acoustic stimulations.

As shown in FIG. 2B, an receiver in the ear 250 is connected to signal processor 216 through cable 252 and connector 254. Receiver in the ear 250 includes a housing 256, which may be a molding shaped to the recipient. Inside receiver in the ear 250 there is provided a capacitor 258, receiver 260 and protector 262. Also, there may a vent shaft 264. Receiver in the ear may be an in-the-ear (ITE) or completely-in-canal (CIC) configuration.

Also, FIG. 2B shown a removable BTE controller 270 directly attached to signal processor 216. BTE controller 270 may also be born worn in a separate device which is connected to signal processor 216 through a suitable communication link. BTE controller 270 includes a display 272 and control buttons 274. In addition, BTE controller 270 may house a power source (not shown), e.g. zinc-air batteries. Signal processor 216 may have an indicator light 276 on earhook 278 to indicate operational status of signal processor 216. Examples of status indications include a flicker when receiving incoming sounds, low rate flashing when power source is low or high rate flashing for other problems.

Returning to FIG. 2A, internal components 244 comprise an internal receiver unit 212, a stimulator unit 226 and an electrode assembly 218. Internal receiver unit 212 comprises an internal transcutaneous transfer coil (not shown), and preferably, a magnet (also not shown) fixed relative to the internal coil. Internal receiver unit 212 and stimulator unit 226 are hermetically sealed within a biocompatible housing. The internal coil receives power and data from external coil 208, as noted above. A cable or lead of electrode assembly 218 extends from stimulator unit 226 to cochlea 232 and terminates in an array 234 of electrodes 236. Electrical signals generated by stimulator unit 226 are applied by electrodes 236 to cochlea 232, thereby stimulating the auditory nerve 238.

In one embodiment of the present invention, array 234 may be inserted in the scala tympani and in the basal region of cochlea 232, e.g. inserted into a depth of up to approximately 2-12 mm. Such a shallow insertion or short array 234 may preserve residual hearing near the apical region of cochlea 232. Array 234 may be inserted into the scala tympani through a cochleostomy adjacent or through the round window (not shown). Other array insertion techniques which preserve residual hearing are also encompassed by embodiments of the present invention. An example of a suitable array 234 is shown in co-pending commonly owned U.S. application Ser. No. 10/518,811, the entire contents and disclosures of which is hereby incorporated by reference. In some embodiments, array 134 may be an endosteal electrode array which is configured for intracochlear but extraluminar insertion. Examples of suitable endosteal electrode arrays 234 are shown in co-pending commonly owned U.S. application Ser. Nos. 10/473,925 and 11/125,171, the entire contents and disclosures of which is hereby incorporated by reference. In other embodiments, array 234 may extend through the basal region using a conventional electrode array, typically up to 22 mm in length, and as shown in U.S. Pat. Nos. 4,532,930, 6,537,200, 6,565,503, 6,575,894 and 6,697,674, which are hereby incorporated by reference herein in their entireties.

In one embodiment, external coil 208 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 212 may be positioned in a recess of the temporal bone adjacent to outer ear 201 of the recipient.

As shown in FIG. 2A, multimodal system 200 is further configured to interoperating with a user interface 280 and an external processor 282 such as a personal computer, workstation or the like, implementing, for example, a hearing implant fitting system. Although a cable 284 is shown in FIG. 2A between implant 200 and interface 280, a wireless RF communication may also be used along with remote 286.

While FIG. 2A shows a multimodal implant in the ipsilateral ear, in other embodiments of the present invention the multimodal implant may provide stimulation to both ears. For example, a signal processor may provide electrical stimulation to one ear and provide acoustical stimulation in the other ear.

Figure 3:
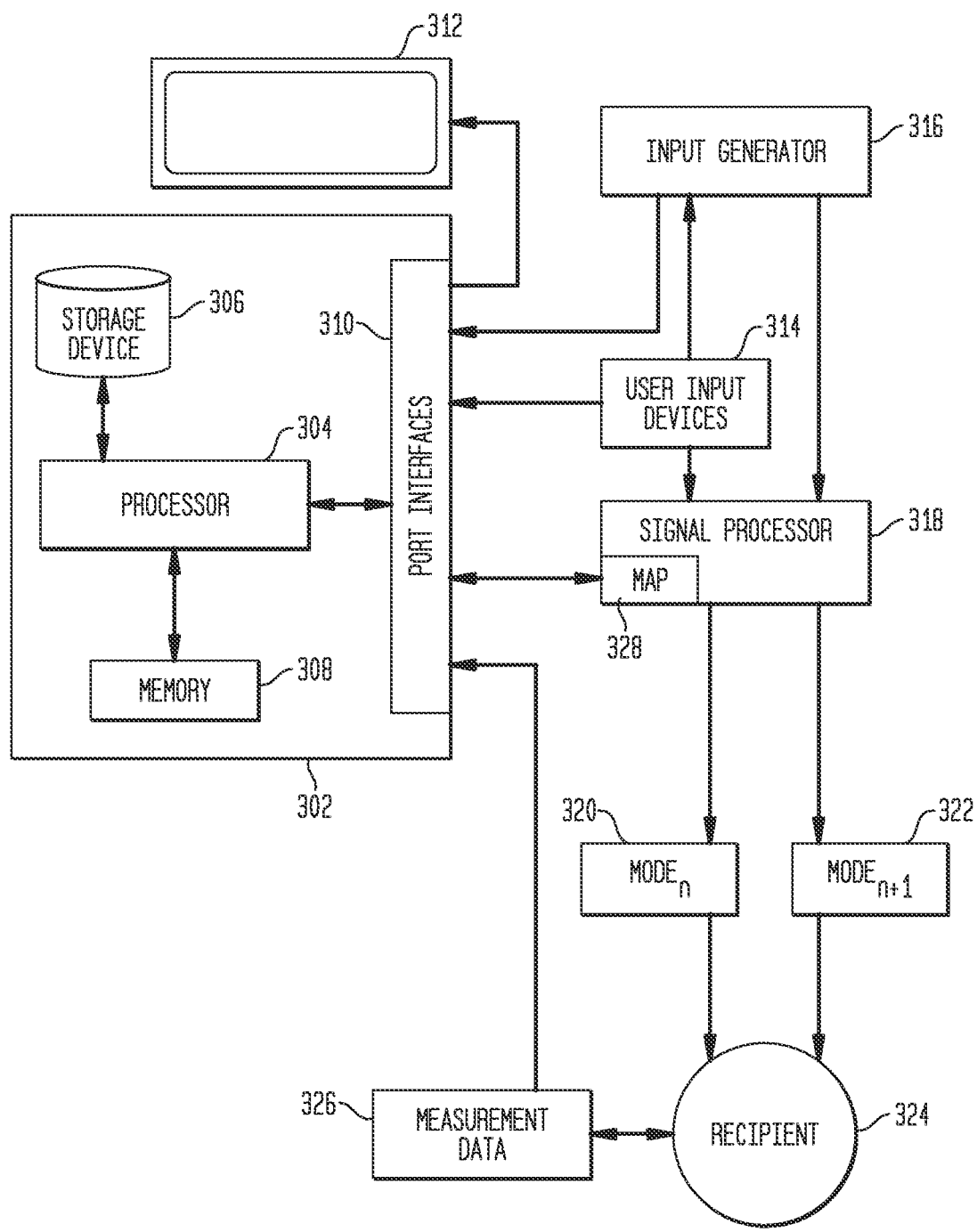
FIG. 3 is a functional block diagram of one exemplary system in accordance with embodiments of the present invention.

Using an exemplary multimodal device shown in FIGS. 2A and 2B, the fitting process that embodiments of the present invention may use is described in the following systems and methods. FIG. 3 is a functional block diagram of one exemplary system of the present invention. FIG. 3 shows a computer 302 having a processor 304, storage device 306, memory 308 and a plurality of port interfaces 310. Note that other common computer components, such as buses, are not shown for clarity. Processor 304 may comprise of plurality of chips. Also there may be different type of port interfaces 310, including serial, parallel, USB, etc. Additional wireless port interfaces 310 may be included. There may be a monitor 312 and user input device 314 connected to computer 302 through port interfaces. A user input device 314 may comprise any combination of devices including keyboards, keypads, mouse, joystick, stylus, etc.

The fitting system in FIG. 3 also shows an input generator 316 that generates an input signal to be administered during the fitting. Note that in some embodiments input generator 316 may be part of computer 302. Input generator 316 is connected to a signal processor 318, which contains storage or memory for the MAP or user-specific program 328. User input devices may be connected to input generator 316 or signal processor 318. Signal processor 318 is connected to $mode_n$ 320 and $mode_{n+1}$ 322. Such stimulus modes 320 and 322 include any process, leading to a quantifiable perception, including acoustic, electrical or mechanical. The stimuli are applied to recipient 324 using modes 320 and/or 322. Using a psychoacoustic measurement technique, measurement data 326 is obtained and provided to the computer 302. In some embodiments, measurement data 326 may be entered using one of the user input devices 314.

The system shown in FIG. 3 may operate as follows. An acoustic input signal generated by input generator 316 is passed to a signal processor 318, which determines transfer functions within the capability of each stimulus mode 320 and 322. The output stimulus for each mode 320 and 322 are generated by the signal processor 318 in accordance with a mode-specific transfer function and any weighting for each mode. At first, each transfer function is a default transfer function or pre-defined transfer function, based on a-priori recipient specific information such as objective or subjective audiograms. Thus, the stimulus mode transfer functions may not be adjusted or weighed from the initial or default transfer function. Upon stimulation, an evoked perception is obtained from recipient 324 and recorded as measurement data 326.

While the stimulation process is occurring, the input signal is also sent to computer 302 to determine a desired perception. Note, in various embodiments, the processing of the input signal by the signal processor 318 and computer 302 may occur in any order or simultaneously. The input signal is processed by microprocessor 304 using a perception model stored on storage device 306. The desired perception may be stored on storage device 306 or in memory 304 and accessed once measurement data 326 of the evoked perception is received. Microprocessor 304 compares desired perception with evoked perception using the loaded perception model. Any discrepancy between the perceptions are translated by microprocessor 304 and sent to signal processor 318 to be stored in MAP 328. For example, the differences in the perceptions in the psychophysical domain may be translated into changes in the signal-processing domain. An adjustment is made by weighting the stimulus mode transfer functions used by the transfer functions of signal processor 318. Psychophysics/transfer function rules from the perception model may be used when optimizing the fitting in response to the outcome of the comparison made by processor 304.

Although the system shown in FIG. 3 has a storage device for the library of perception models, in other embodiments the library of perceptual models may be updated or the library may consist of a network of computers. Such further embodiments provide a library of perceptual models allowing the system to be updated as new perception models are created. Also, the library allows devices to change signal processing strategies without the need to re-train specialists to fit a device in accordance with the new strategy.

Systems of the present invention may have particular application in a device involving electro-acoustic stimulation using a multimodal prosthesis device. In such applications, normal hearing loss leaves residual acoustic hearing capability in low frequencies, while requiring electric stimulation at higher frequencies. System may provide for significantly easier determination of an appropriate cut-off, transition and balance, e.g. dB, SPL, and μA, between acoustic stimulation and electrical stimulation.

A plurality of different types of input signals may be applied in embodiments of the present invention. For example, the input signal may comprise one or more of the following: music, speech, a quiet signal, a loud signal and a signal within a limited frequency band. During fitting multiple input signals may be used with embodiments of the present invention to optimize the stimulus mode weighting for several different types of input signals. Furthermore, the input signal may be randomly manipulated by means of digital signal processing to analyze the change in evoked perceptions.

Some input signals may be complex to better represent real live sounds. For example, the phoneme mismatch matrix may be used to adjust the electrical and acoustical stimulation as set out in European Patent No. 1,338,301, the entire contents and disclosure of which is hereby incorporated by reference. Other input signals may be harmonic sounds, low frequency, or high frequency sounds.

Still other input signals may comprise signals that generate deterministic and measurable perceptions. For example, such embodiments may comprise systematically varying the bandwidth of an input signal and monitoring the resulting loudness change. Additionally or alternatively, real-life sound samples may be applied, for example as set out in *Real-Life-Fitting: Adjustment of hearing aids to real-life situations*, AudioCare AG, Pratteln, Switzerland, the entire contents and disclosure of which is hereby incorporated by reference.

In some embodiments of the present invention may comprise presenting input signals that sweep along the iso-loudness lines, and checking for changes in loudness, which should be minimum and monotonous for a good fitting.

Generally there are two techniques for obtaining an evoked perception from the recipient, namely, a subjective psychoacoustic technique and an objective psychoacoustic technique. The subjective technique involves obtaining from the recipient a measure of evoked perception caused by the stimulus may comprise accepting from the recipient a subjective indication of the evoked perception. These subjective psychoacoustic measurements provide a suitable method for capture perceptions from adult recipient. In obtaining the subjective measurement of loudness, the recipient may respond to a structured conversation with a clinician or by interaction with a software interface. For example the recipient may input a selection from the list of inaudible, threshold, soft, medium, comfortably loud and uncomfortably loud. Additionally or alternatively the recipient may input a selection from the list of harsh, tinny, dull and garbled. Other scales, corresponding to the selected perceptual model might be used. More complex models might include questionnaire type recipient responses.

Additionally or alternatively, the evoked perception or recipient response may be obtained by means of objective measurement technique, such as measurement of an evoked compound action potential of the auditory nerve or longer latency responses, including bilateral, cortical and mismatched potentials. An objective measurement is particularly useful for automating the fitting and in some embodiments the measurement may be done by a computer. Such a measurement could, for example, be obtained by the neural response telemetry (NRT™) technique described in International Publication No. WO2002/082982, the entire contents and disclosure of which is hereby incorporated by reference. Other objective measurements including imaging the insertion depths of the electrodes from the electrical mode. Such objective measurements would be particularly suitable in case of a non-cooperative hearing impaired recipients or young recipients. Normal input-output functions, i.e. objective response models would be used instead of the perceptual model, to define a desired objective response associated to a given input signal. Also the objective measurements may be used in combination with subjective measurements.

The present invention will now be described with reference to the following exemplary method embodiments. Such method embodiments may use any of the multimodal device or system features described in this application.

Figure 4:
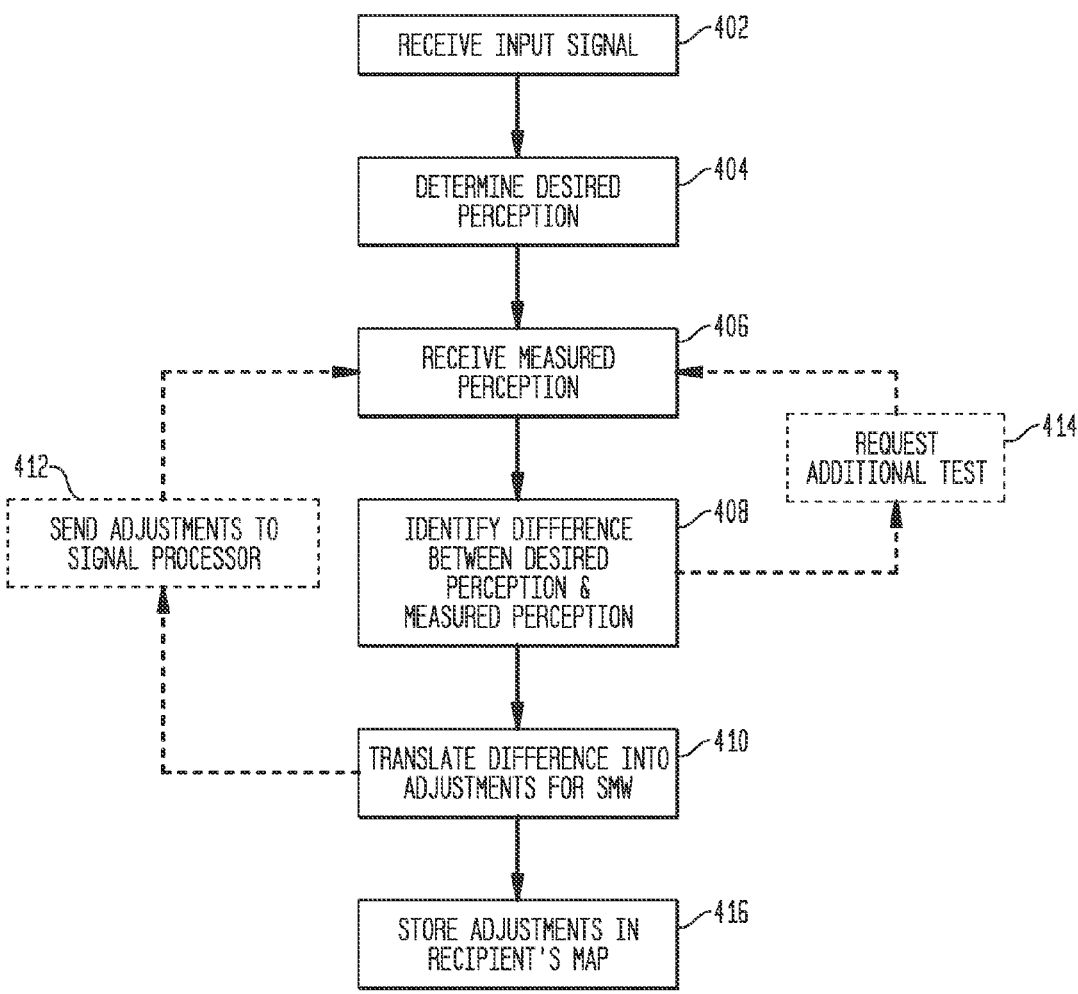
FIG. 4 is a flowchart illustrating a fitting procedure in accordance with embodiments of the present invention.

FIG. 4 is a flowchart illustrating a method of one embodiment performed by the computer program product implemented in an exemplary system. In 402 the program receives an input signal that is selected. The program passes the input signal through a selected psychophysics transfer function or perceptual model from a library of perceptual models to determine a desired perception in 404. The desired perception may be quantified by loudness and measured in sones or categorial loudness units. The desired perception is a target perception of what a normal hearing person would perceive or what is known to optimise efficiency of the hearing system based on the selected perceptual method. In 406 the program receives an input of the measured evoked perception in sones. The input may be determined by objective methods or subjective psychoacoustics techniques. Upon receipt of the evoked perception the program is able to identify the difference between the desired perception and measured perception in 408. Any difference in sones between the desired perception and evoked perception is translated in 410 into adjustments required for the weighting the stimulus mode transfer function. The changes in the stimulus mode weighting are done to reduce the difference between the evoked perception and measured perception. The adjustments may be controlled using rules from the perceptual model that was used to determine the desired perception. In some embodiments, the program in 412 may send the adjusted to weigh the stimulus mode transfer functions to the signal processor, which provides a new stimulation signal to the recipient of the same input. The differences are further refined by making necessary adjustments and repeating the process. Alternatively, in some embodiments, the program may test the same input signal in 414 without making adjustments or weighting to the stimulus mode transfer functions. Once a satisfactory adjustment is made or evoked perception is made the program in 416 stores the adjusted values in the recipient's MAP or user-specified program. The program may continue fitting the recipient using a different input signal and repeat a similar process.

As shown by the steps in FIG. 4, the adjustments to stimulus mode transfer functions are done so that the changes to the evoked perception would substantially match or equate to the desired perception. The adjustments may be re-tested using the same input signal and obtaining a new evoked perception which is compared with the original desired perception. Additionally steps and embodiments are described in the following flowcharts.

Figure 5:
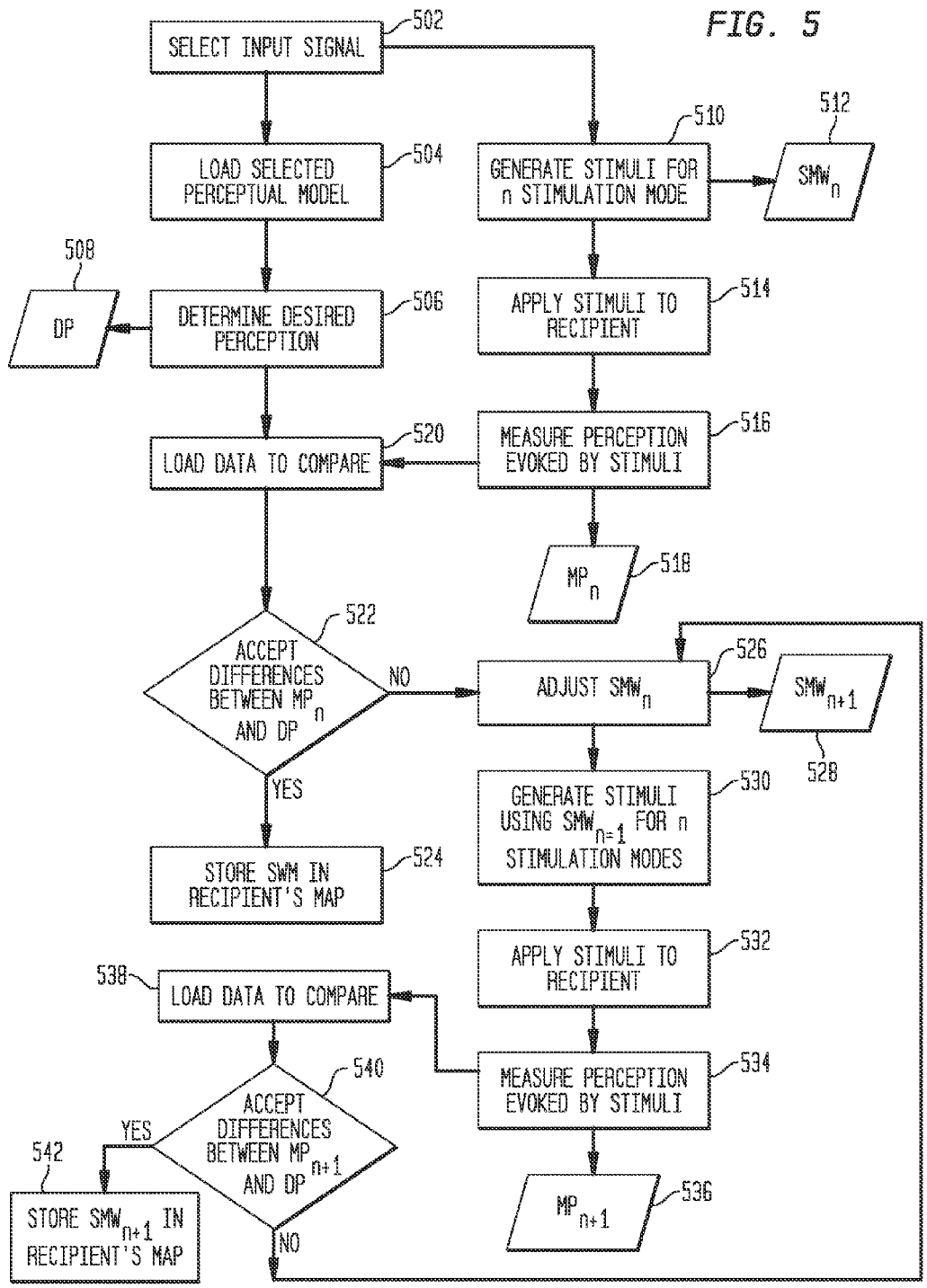
FIG. 5 is a flowchart illustrating a fitting procedure using adjusted stimulus mode weightings.

FIG. 5 is a flowchart illustrating the various steps used when adjustments to the stimulus mode weighting is made using an iterative embodiment of the present invention. It should be appreciated that the stimulus mode weighting (SMW) adjust the stimulus transfer functions. In 502 an input signal is selected by the clinician or the computer program. In 504 a perceptual model is loaded into the computer program.

The model in 506 determines the target or desired perception from the input signal and stores it as desired perception (DP) data 508.

In conjunction, the input signal is also sent to one or more signal processors in 510 to generate stimuli for number of stimulation modes used by the multimodal system. In some embodiments one signal processor may be able to generate stimulation signals for different modes (acoustic, electrical or mechanical stimulation). Other embodiments may have independent signal processors for each mode. In either case, the stimuli are generated according to transfer functions of the signal processors. Stimulus mode transfer function may be adjusted for each of the various modes by adjusting the stimulus mode weighting. Stimulus mode weighting defines the parameters of how the signal processor modifies the input signal using a transfer function to generate the stimuli for each mode of the multimodal device. It should be appreciated that there are different weightings may be applied to the stimulus mode transfer functions for various input signals. In the initial step, each mode may have default values selected by the manufacturer of the multimodal device. These are initially are stored as $SMW_n$ data 512. It should be understood that on the initial test of an input signal, the $SMW_n$ data would be same as the transfer functions of the signal processor or default values.

Next in 514, the stimuli are applied to the recipient using various components that comprise each mode. In 516, the recipient's perception evoked by the stimulation is measured and stored as measured perception ($MP_n$) data 518. The data may be entered manually when using subjective psychoacoustic techniques or automatically when using objective psychoacoustic techniques.

Once $MP_n$ data 518 is stored, the computer program product in 520 loads the DP 508 and $MP_n$ data 518. The differences between DP and $MP_n$ data are compared and in 522 the computer program product determines whether those differences are acceptable. It should be appreciated to those of skill in the art that certain differences between the DP and $MP_n$ may be tolerated. The clinician may rely on the methods or systems of the present invention to identify these differences that are outside of a pre-defined tolerance range. In other embodiments, there may be a manual override when a difference is identified as acceptable by the clinician. In an ideal setting the DP and $MP_n$ should equate or at least substantially match.

Assuming that the differences are acceptable, based on the rules defined by a perceptual model or an input from the audiologist, $SWM_n$ data 512 generated in 510 is stored in the recipient's MAP in 524 and the process for fitting that input signal ends. Note that if no changes are made, default values may be stored. A difference may be acceptable if the difference is less than a pre-defined range by the perceptual model. While a result of DP data equaling $MP_n$ data would be acceptable, an acceptable result may also be one where the DP data approximately equals the $MP_n$ data. Further fitting may continue for additional input signals.

In 522 if the differences are not acceptable, the $SMW_n$ previously used is adjusted in 526. In general the adjustment may involve translating the difference between the DP and $MP_n$ into a value that alters one parameter transfer function for at least one of the modes. In some embodiments, each mode of the multimodal implant may be altered. One method for adjusting is described further in FIG. 6 below. The adjusted result in 526 is stored as $SMW_{n+1}$ data 528. Using $SMW_{n+1}$ data 528 the signal processor(s) generates new stimuli for each mode in 530 using the input signal and applies the stimuli in 532. In 534, the recipient's perception evoked by the additional adjusted stimulation is measured and stored as $MP_{n+1}$ data 536.

To compare with the DP 508, the computer program in 538 loads the DP 508 and $MP_{n+1}$ 508 data. The differences between DP 508 and $MP_{n+1}$ 528 data are again compared and in 540 the computer program product determines whether those differences are acceptable. Assuming that the differences are acceptable, the $SWM_{n+1}$ 508 data generated in 526 is stored in the recipient's MAP in 542 and the process for fitting that input signal ends. Further fitting may continue for additional input signals. An unacceptable result may be further refined by repeating the adjustment steps and returning to step 526.

Figure 6:
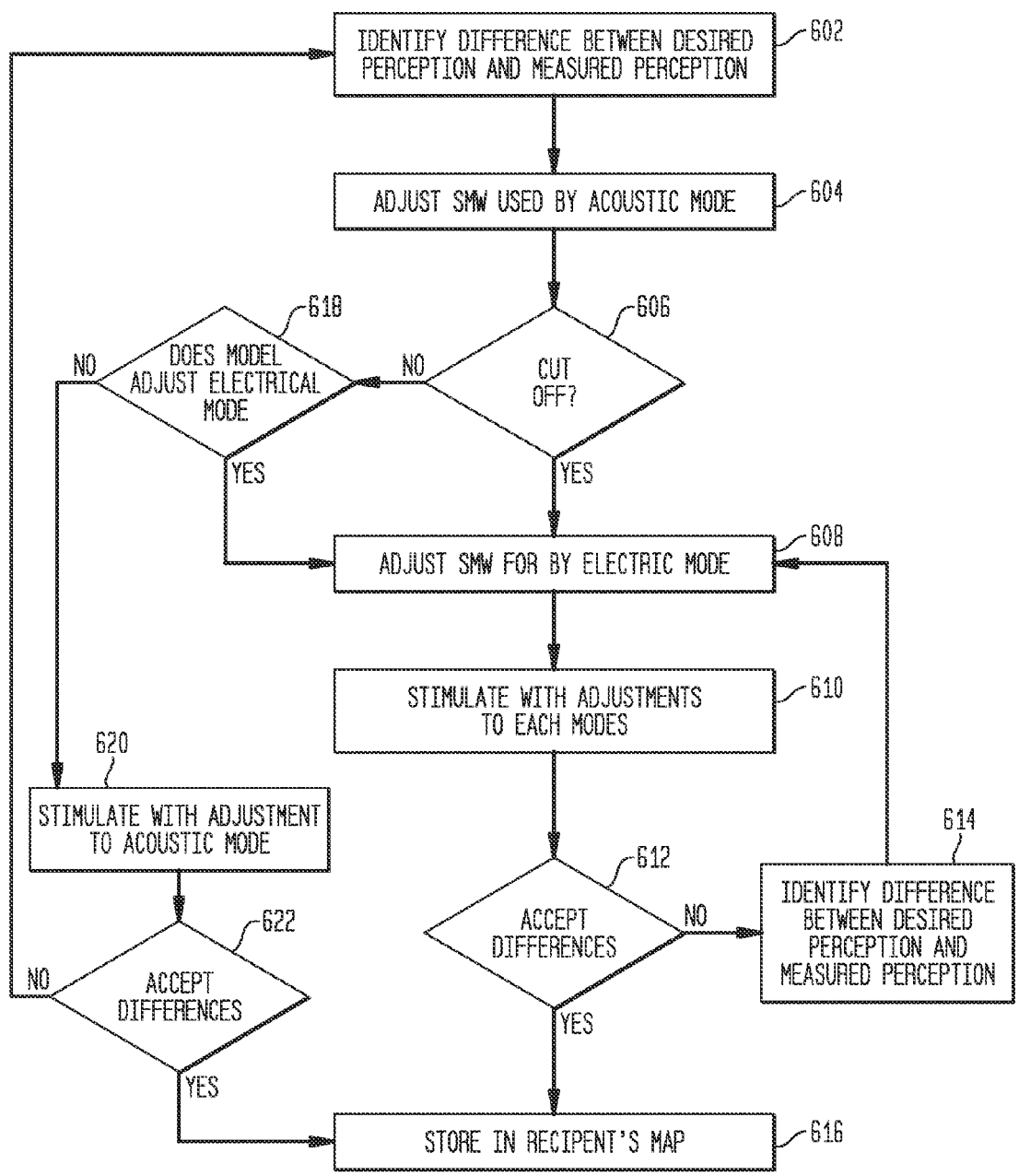
FIG. 6 is a flowchart illustrating the cut off for adjusting stimulus mode weightings.

The adjustment necessary to the measured perception converges towards the desired perception may involve changing, through weighting, various stimulus mode transfer functions so that the signal processor may produce a different stimulus. The adjustments may be derived from one or more perceptual model. FIG. 6 is a flowchart illustrating one embodiment of the adjustment process. In 602 the system or computer program product identifies a difference between a desired perception and a measured perception that is unacceptable. The difference is translated from values used to measure the perception, e.g. sones, to a value suitable for adjusting stimulus mode transfer functions. In 604 an adjustment to the stimulus mode weighting for the acoustic mode is made. This adjustment may be done by increasing the gain, thereby increasing the loudness. In 606, the acoustic mode may have a cut-off or maximum at which an increase in the gain is not effective or possible using the acoustic mode. In some perceptual modes, there may be a balance cut-off which is not the maximum, but is a point at which benefits of the acoustic mode would not compensate for the difference between the desired perception and measured perception. When the adjustment made in 604 exceeds the limit in 606, the system stops increasing the stimulus mode weighting of the acoustic mode and begins in 608 to adjust the stimulus mode weighting of an electrical mode. This may be done by translating the difference from the cut-off and the desired perception into a value suitable to the stimulus mode weighting of the electrical mode, i.e. gain, voltage, current, frequency. In 610 the input signal is tested again using the adjusted acoustic and electrical stimulus mode weighting. Again, the system determines if the adjusted results produce a difference that is acceptable in 612. If not, the system continues by identifying the difference between the desired perception and measured perception in 614. At this point the system knows the cut-off for the acoustic mode was previous reached so the system continues by adjusting stimulus mode weightings for the electrical signal in 608. This refinement loop continues until the difference is acceptable and the stimulus mode weighting is stored in recipient's MAP in 616.

Return to cut-off decision 606, when the cut-off is not reached and the difference between the desired perception and the measured perception is compensated with adjustments to the acoustic mode, the system proceeds 618. In 618 the system checks the rules of the perceptual model to determine whether stimulus mode weighting of the electrical mode should be adjusted. When yes, the system moves to 608 and assumes that the acoustic mode is satisfied. When the electrical mode is not used, the system stimulates the recipient with the adjusted stimulus mode weighting for the acoustic mode in 620. The differences between the perceptions are determined to be acceptable in 622. When not acceptable the process loops back to 602 to repeat the adjustment process.

When acceptable in 622, the process stores the adjusted stimulus mode weighting in the recipient's MAP in 616.

While FIG. 6 is described in context with a multimodal device that uses acoustic and electrical modes, it should be appreciate that the adjustment steps may be suitable for other combinations of modes. Also, while the acoustic mode is adjusted first in FIG. 6, in other embodiments adjust the various modes in any order.

The cut-off shown in FIG. 6 may be the maximal gain for a mode of the multimodal device and no increase will contribute to a hearing perception. This cut-off limit or maximal gain may be derived from models, such as the "dead regions theory" described in Moore et al, "A test for the diagnosis of dead regions in the cochlea," Br J Audiol. Vol. 34 (2000) pages 205-224, the entire contents and disclosures of which are hereby incorporated by reference.

Figure 7:
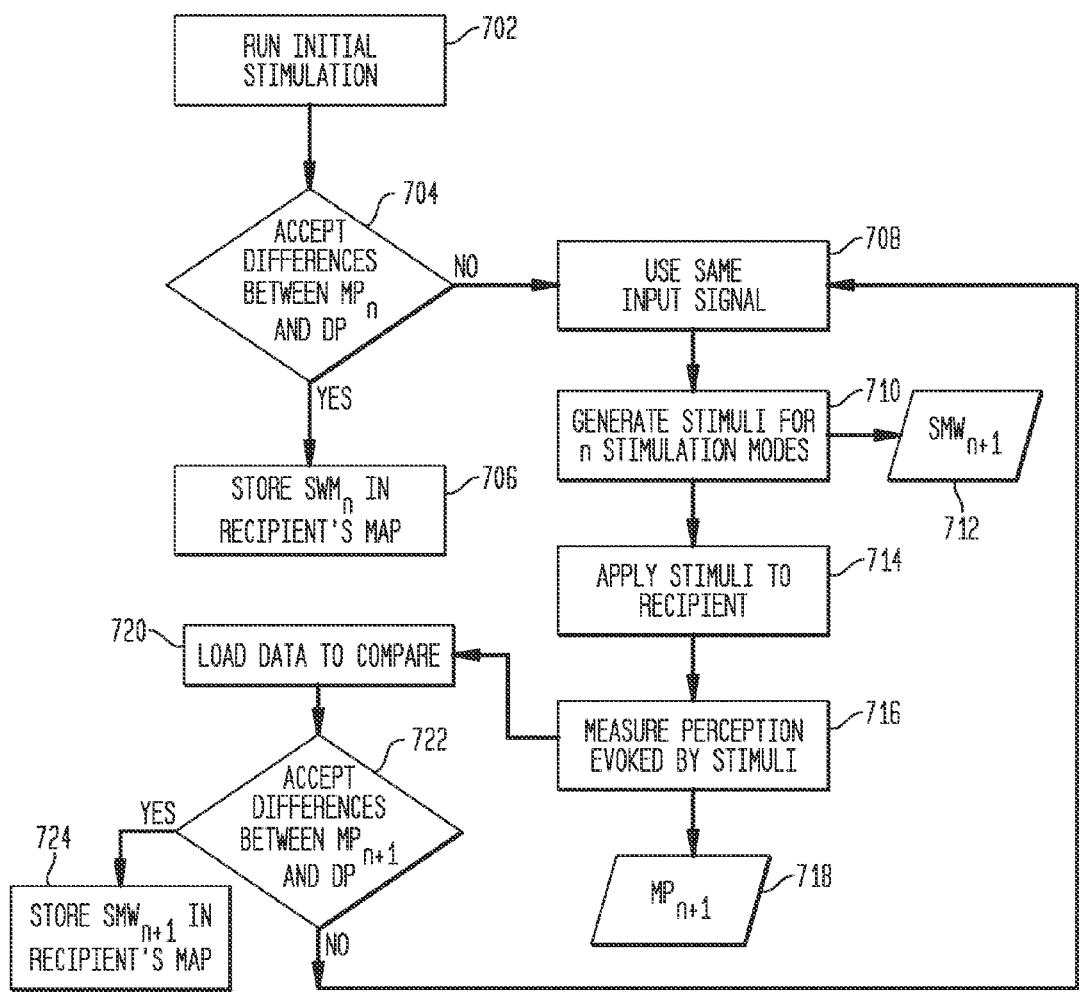
FIG. 7 is a flowchart illustrating a fitting procedure that repeatedly uses the same input signal.

FIG. 7 illustrates a flowchart where the input signal is administered and the evoked perception from multiple data sets is compared against the desired perception. To begin in 702, the process performs the initial steps 502-520 identified in FIG. 5. The differences between DP and $MP_n$ data are compared and in 704 the process determines whether those differences are acceptable. Acceptable results are stored in the recipient's MAP in 706 and the process to fit that input signal ends. Further input signals may be fitted using a similar process.

When in 704 the differences are unacceptable, the process uses the same input signal in 708 and without adjustment from a perceptual model and generates stimuli for each of the stimulation modes in 710. The stimulus mode weighting are stored as $SMW_{n+1}$ data 712. The generated stimuli are applied in 714 to the recipient and the recipient's perception evoked by the stimulation is measured in 716 and stored as measured perception ($MP_{n+1}$) data 718. It should be noted that a different measurement technique than the initial steps 702 may be used to capture the perception evoked by the recipient in 716. In 718 the process loads the DP data from the initial steps 702 to compare with the $MP_{n+1}$ data. Similar to previously described methods, in 722 an acceptable difference between DP data and $MP_{n+1}$ data is assessed. When no difference is found or the difference is accepted, the stimulus mode transfer functions are stored in the recipient's MAP in 724. When the difference is not acceptable in 722, the process may repeat with step 708, or the process may adjust the weighting of the stimulus mode transfer functions as described in other embodiments of the present invention.

In some embodiments of the present invention may combine the iterative process shown in FIG. 5 along with the multiple tests of an evoked perception in FIG. 7 in various combinations. For example, an input signal might be tested twice with the iterative process with a subjective measurement of the evoked perception as shown in FIG. 5 and then verified using an objective measurement of the evoked perception as shown in FIG. 7. Another example may involve first testing a recipient with different psychoacoustic techniques as shown in FIG. 7 and then proceeding to the iterative fitting in FIG. 5.

Figure 8:
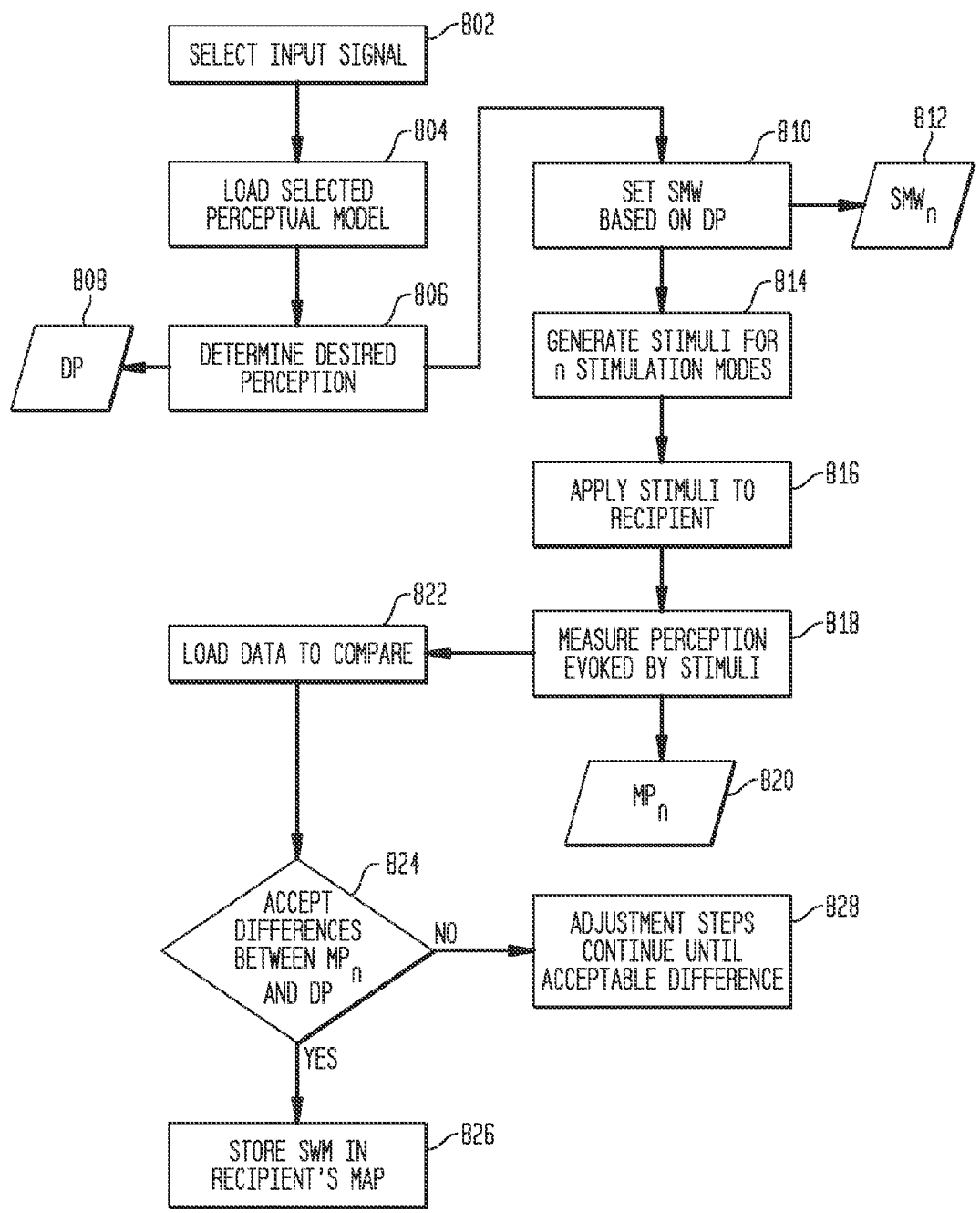
FIG. 8 is a flowchart illustrating a fitting procedure that adjust the stimulus mode weightings without receiving an evoked measurement.

In one embodiment of the present invention, the method may involve adjusting the stimulus mode weighting prior to measuring the evoked response. Such embodiments are particularly suited to real-time weight adjustments or when no measurement technique of the evoked response is available. For real-time application the embodiments of the present invention may be part of a signal processor. FIG. 8 illustrates a flowchart where the stimulus mode transfer functions are adjusted using stimulus mode weighting (SMW) to the desired perception model prior to stimulating the recipient. In 802 an input signal is selected by the audiologist or the computer program. In 804 a perceptual model is loaded into the computer program. The model in 806 determines the target or desired perception from the input signal and stores it as DP data 808. Next, unlike other embodiments, in 810 the stimulus mode weighting are adjusted prior to stimulating the recipient and stored as SMW data 812. In 814 the process generates stimuli based on the $SMW_n$ data 812 for number of stimulation modes used by the multimodal device.

To verify the effectiveness of the stimuli during stimulation in 816, the recipient's perception evoked by the stimulation may be measured in 818 and stored as $MP_n$ data 820. In 822, the process loads the DP data 808 to compare with the $MP_n$ data 820. Similar to previous methods in 824 an acceptable difference between DP data 808 and $MP_n$ data 820 is accessed and made. When no difference is found the stimulus mode weighting are stored in the recipient's MAP in 826. When the difference is not acceptable in 824, the process may repeat by further adjusting the stimulus mode weighting in 828. This further adjustment may continue until the recipient's MAP is updated in 826, as described with the above embodiments.

One advantage of presenting an initial stimulation signal with adjusted stimulus mode transfer functions, is that such an embodiment may shorten the refinement steps necessary for certain input signals.

Figure 9:
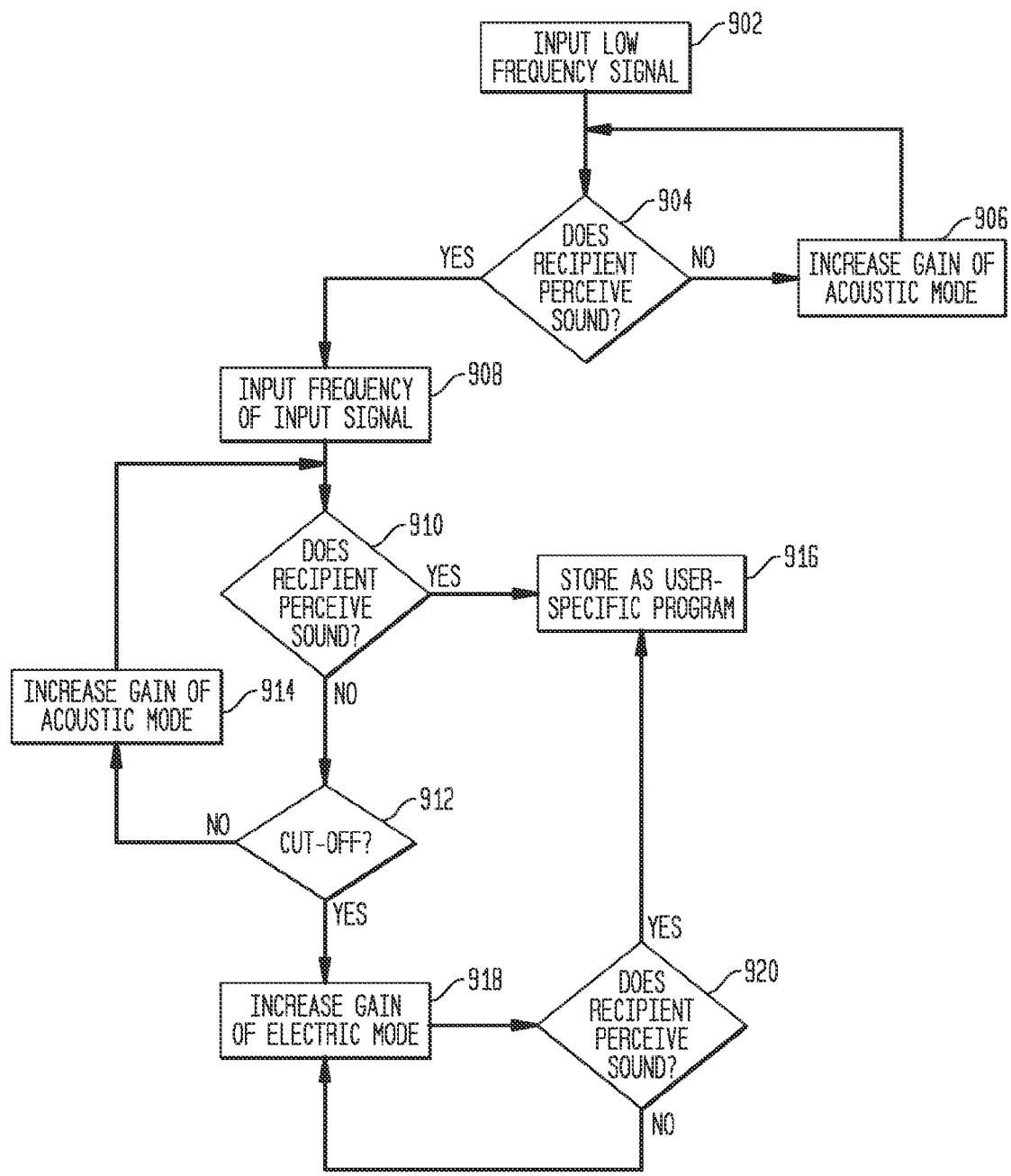
FIG. 9 is a flowchart illustrating fitting using a low and high frequency input signal in accordance with one embodiment of the present invention.

Another embodied method of fitting a multimodal device is shown in FIG. 9. FIG. 9 is a flowchart illustrating a method using a model for electro-acoustic stimulation, i.e. using a system which includes aspects of a conventional prosthetic implant and aspects of a hearing instrument. In this fitting embodiment, the system starts with a low-frequency input signal in 902. Optimal fitting over all system gain per frequency might be established by presenting a pulsating low-frequency noise, e.g. a signal centered around 125 Hz at 40 dB SPL. In 904 the recipient's evoked perception is measured to determine whether the input signal is perceivable. When no sound is perceived, in step 906, the frequency specific gain of the acoustic stimulator mode is increased and step 904 repeats until the recipient indicates to just notice the sound. Note that during this time, the gain for the electric stimulation remains zero. When the sound is perceived in 904, the centre frequency of the input signal is increased in 908, e.g. to 500 Hz. Again, the recipient in 910 indicates when the increased input signal is perceived. When no perception is made, the system first checks to determine whether the maximal gain or cut-off is reached for the mode in 912. If not, the system proceeds to 914 and increases the gain of the acoustic mode. The perception of the recipient of is measured again in step 910. Once the recipient perceives the sound in 910 the values are stored in a user-specific program in 916. However, if in 912 the cut-off is reached, then the system proceeds to 918 to increase the gain of the electrical mode. Next, in 920 the recipient's perception is measured and when no perception is made, the system again increase the electrical mode in 918. Once the recipient perceives the sound in 920 the values are stored in a user-specific program in 916. This procedure is repeated for multiple input frequencies and sound pressure levels.

The adjustment to the electrode mode may be done as follows. For example using a low frequency tone that is audible via acoustic amplification, the program may shift the electrode used for presenting the upper frequency component to match harmonics in response to the evoked perception. In addition, for example, the center of the electrical stimulation for a given frequency may be shifted along the basilar membrane by varying the degree of current distribution between at least two electrodes.

Once the fitting process is completed, the adjustments are stored to the recipient's signal processor as a user-specific program or in a MAP. Thus, when the recipient is using the multimodal implant, the sound signals that are received will be transferred to the modes using the adjustments. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All documents, patents, journal articles and other materials cited in the present application are hereby incorporated by reference herein.

EXAMPLE

The present invention will now be described by way of the following example.

A 1 kHz Hz ⅓ octave noise with the equivalent input level of 70 dB SPL is fed into an electro-acoustic sound processor. The electro-acoustic sound processor has an acoustic mode, hearing instrument, and electrical mode, electrode array. The selected perception model is the ISO 532 (Zwicker model). According to ISO 532 model the input signal should translate into a loudness of 8.8 sones for a normal hearing person. The recipient's response gives 4.9 sone, which is translated into a gain loss of 10 dB according the perception model. To compensate this gain loss, the fitting system increases the gain of the hearing instrument transfer function accordingly. However, the hearing instrument reaches a maximum gain after increasing for 5 dB. Thus, the system starts electrical stimulation in addition and increases the electrical stimulation current until the recipient perceives the signal at a loudness of 8.8 sone. The adjustments, or the weighting of the stimulus mode transfer functions, to the hearing instrument's electrode array are stored as a user-specific program for use.

What is claimed is:

1. A system for fitting a multimodal hearing system to a recipient comprising:
    two or more of the following devices configured to deliver stimulation signal sets to the recipient corresponding to an input signal according to stimulus mode weightings, respectively, wherein at least two of the two or more devices provide different modes of stimulation:
        a mode-E device configured to provide an electrical mode of stimulation;
        a mode-A device configured to provide an acoustic mode of stimulation produced by an electro-acoustic transducer included therein;
        a mode-M device configured to provide a mechanical mode of stimulation, and
        a mode-P device configured to provide a photo effect mode of stimulation;
    an input device for obtaining a measurement of a perception evoked by applying to the recipient the two or more stimulation signal sets, wherein at least two of the two or more stimulation signal sets are for different stimulation modes; and
    a processor for adjusting one or more of the stimulus mode weightings based on the difference between the measured evoked perception and a desired perception for the input signal.

2. The system of claim 1, wherein the desired perception is determined using a perceptual model.

3. The system of claim 2, wherein the perceptual model is selected from a library of perceptual models.

4. The system of claim 1, wherein the desired perception is determined using an input-output model of an objective evoked response.

5. The system of claim 4, wherein the input-output model is selected from a library of input-output models.

6. The system of claim 1, wherein the multimodal hearing system further comprises memory for storing the adjusted stimulus mode weighting.

7. The system of claim 1, wherein the two or more stimulation mode devices include the mode-A device.

8. The system of claim 1, wherein the two or more stimulation mode devices include the mode-E device.

9. The system of claim 1, wherein the two or more stimulation mode devices include the mode-M device.

10. The system of claim 1, wherein the two or more stimulation mode devices include the mode-P device.

11. The system of claim 1, wherein:
    the processor for adjusting the stimulus mode weightings is a first processor; and
    the system further comprises:
        a second signal processor for generating the two or more stimulation signal sets.

12. The system of claim 8, wherein:
    the mode-E device includes an electrode array configured for at least one of insertion into and near the cochlea.

13. The system of claim 9, wherein:
    the mode-M device includes an actuator configured to be coupled to a structural aspect of the inner ear fluid system so as to transfer vibrations thereto.

14. The system of claim 11, wherein:
    the second signal processor is configured to generate the two or more stimulation signal sets based on two or more stimulation mode transfer functions, respectively.

15. The system of claim 14, wherein:
    the two or more stimulation mode transfer functions correspond to the stimulus weightings, respectively; and
    the second signal processor is configured to adjust the two or more stimulation mode transfer functions according to the corresponding stimulus mode weightings, respectively.

16. The system of claim 14, wherein:
    the first processor is configured to alter the one or more of the stimulus mode weightings by altering at least one of gain, compression and attack time for at least one of the two or more stimulation modes.

17. The system of claim 16, wherein:
    the first processor is further configured to alter the gain by at least increasing the gain.

18. The system of claim 14, wherein:
    the first processor is configured to alter the one or more of the stimulus mode weightings by altering the frequency of one of the two or more stimulation devices.

19. The system of 18, wherein:
    the first processor is further configured to alter the frequency by at least increasing the frequency.

20. The system of claim 1, wherein:
    the signal processor is further configured to store the adjusted stimulus mode weightings in a user-specific MAP.

21. The system of claim 1, wherein:
    the processor, in cooperation with the two or more devices and the input device, is configured to adjust iteratively.

* * * * *